United States Patent [19]

Zawalski

[11] Patent Number: 4,925,993
[45] Date of Patent: May 15, 1990

[54] PROCESS FOR PREPARING CHLOROFLUOROCARBONS VIA AN IN SITU GENERATED ACTIVATED ALUMINUM TRICHLORIDE CATALYST AND PRODUCTS RESULTING THEREFROM

[75] Inventor: Robert C. Zawalski, Houston, Tex.

[73] Assignee: Dixie Chemical Company, Pasadena, Tex.

[21] Appl. No.: 366,769

[22] Filed: Jun. 14, 1989

[51] Int. Cl.$^5$ .................. C07C 17/24; C07C 17/20; C07C 19/08; B01J 31/00
[52] U.S. Cl. .................................. 570/151; 502/151
[58] Field of Search ..................... 570/151; 502/151

[56] References Cited

U.S. PATENT DOCUMENTS

| | | | |
|---|---|---|---|
| 2,598,411 | 5/1952 | Miller et al. | 570/151 |
| 2,924,579 | 2/1960 | Young | 502/151 |
| 4,748,284 | 5/1988 | Gozzo et al. | 570/151 |

FOREIGN PATENT DOCUMENTS 1668346 3/1973 Fed. Rep. of Germany .

OTHER PUBLICATIONS

Miller et al., "J. Am. Chem. Soc.", vol. 72, (Feb. 1950), pp. 705–707.
Okuhara, 43 J. Org. Chem. 2745 (1978).

*Primary Examiner*—J. F. Evans
*Attorney, Agent, or Firm*—Pravel, Gambrell, Hewitt, Kimball & Krieger

[57] ABSTRACT

A process of isomerizing a chlorofluorocarbon of the formula:

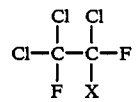

wherein X is chlorine or fluorine to the compound of the formula:

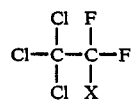

The process comprises contacting the chlorofluorocarbon with an activated aluminum trichloride catalyst. The catalyst is prepared by contacting the chlorofluorocarbon with anhydrous aluminum trichloride in the presence of a metal. The metal is selected from the group consisting of stainless steel, chromium, manganese, molybdenum, tungsten and combinations thereof.

32 Claims, No Drawings

PROCESS FOR PREPARING CHLOROFLUOROCARBONS VIA AN IN SITU GENERATED ACTIVATED ALUMINUM TRICHLORIDE CATALYST AND PRODUCTS RESULTING THEREFROM

FIELD OF THE INVENTION

This invention relates to activated aluminum trichloride catalysts and the process of isomerizing chlorofluorocarbons in the presence of such catalysts. The use of the catalyst in the process renders a reaction mixture having less than 450 ppm of non-isomerized material.

BACKGROUND OF THE INVENTION

Chlorofluorocarbons have been widely used in industry as refrigerants and aerosols. When released into the atmosphere, the accumulation of such chlorofluorocarbons can eventually cause depletion of the ozone layer. Many countries have barred the use of $CCl_2F_2$ and $CCl_3F$ due to their ability to reach the stratosphere. The industry has focused on the use of perfluorocarbons, tetrafluoroethanes and chlorofluorohydrocarbons in recent years since these compounds are believed not to significantly contribute to ozone depletion. Of particular interest to the refrigerant industry is 1,1,1, 2-tetrafluoroethane. Such compounds can be derived from the intermediates 1,1-difluorotetrachloroethane, 1,1,1-trifluorotrichloroethane and 1,2,2,2-tetrafluorodichloroethane. These intermediates are, in turn, the isomers of the more readily obtainable chlorofluoroethanes 1,2-difluoro-1,1,2,2-tetrachloroethane, 1,1,2-trifluoro-1,2,2-trichloroethane and 1,1,2,2-tetrafluoro-1,2,-dichloroethane, respectively.

The isomerization of such chlorofluoroethanes by treatment with aluminum trichloride is well documented in the art. For example, Okuhara in 23 *J. Org. Chem* 2745 (1977) reports the use of aluminum trichloride and an inert solvent for isomerizing 1,1,2-trichloro-1,2,2-trifluoroethane. Unfortunately, the prior art methods render an unsatisfactory amount of starting material in the final reaction mixture. This is evidenced in, for example, German Pat. No. 1,668,346 which discloses an isomerization method for the production of 1,1,1-trifluorotrichloroethane. This process involves the preactivation of an aluminum chloride catalyst with 1,1,2-trifluorotrichloroethane at 30° to 60° C., subsequent cooling and then addition of new starting material. The amount of starting material in the final reaction mixture is from about 2% to 10%. As the boiling point of starting material and the desired isomerized product are roughly the same, conventional distillation techniques can not be employed to separate the compounds.

Alternative methods for obtaining the isomerized product with negligible amounts of non-isomerized starting material are therefore needed.

SUMMARY OF THE INVENTION

The invention comprises a process of isomerizing chlorofluoroethane intermediates of 1,1,1,2-tetrafluoroethane. The process comprises contacting the chlorofluorocarbon with an activated aluminum trichloride catalyst. The amount of non-isomerized chlorofluorocarbon in the product mixture is generally less than 450 ppm.

The activated aluminum trichloride catalyst employed in the reaction is generated in situ from a first isomerization reaction of chlorofluoroethanes in the presence of anhydrous aluminum trichloride and a metal. This reaction may be conducted in a stainless steel reaction vessel whereby the requisite metal is leeched from the vessel itself. Conversely, metal powder or a metal selected from the group consisting of chromium, manganese, molybdenum, tungsten and combinations thereof, may be added directly to the reaction vessel. During catalyst activation, the isomerization proceeds until the amount of non-isomerized chlorofluoroethane in the product mixture is less than about 10,000 ppm. Removal of the product mixture renders the desired activated catalyst.

DESCRIPTION OF THE PREFERRED EMBODIMENTS

The invention is drawn to a process of isomerizing a chlorofluorocarbon useful as an intermediate in the production of 1,1,1,2-tetrafluoroethane. Preferably, the invention is drawn to the isomerization of a chlorofluorocarbon of the formula:

wherein X is Cl or F, to the product of the formula:

The process comprises contacting the chlorofluorocarbon with an activated aluminum trichloride catalyst. The chlorofluorocarbon is most preferably $CCl_2FCClF_2$.

PREPARATION OF THE ACTIVATED CATALYST

The activated aluminum trichloride catalyst is in situ generated by contacting a chlorofluorocarbon intermediate of 1,1,1,2-tetrafluoroethane, preferably a compound represented by formula (I), most preferably the compound wherein X is F, with anhydrous aluminum trichloride in the presence of a metal. The weight ratio of chlorofluorocarbon to aluminum trichloride is approximately between from about 16:1 to about 150:1, most preferably 30:1.

The reaction may be conducted in a glass vessel with a small amount of finely divided powdered metal added. The metal component is selected from stainless steel or chromium, manganese, molybdenum, tungsten and combinations thereof. The mesh of the metal normally ranges from about −200 to about −300. Preferably a mixture having a weight ratio of 99:1 to 1:99, particularly 1:3 to 3:1, is employed. Most preferably, the mixture comprises chromium and manganese. The aluminum trichloride : metal weight ratio is between from about 200:1 to 2000:1; most preferably about 600:1.

Alternatively, the reaction may be conducted in a stainless steel vessel wherein the requisite metal is leeched into the reaction vessel.

The reaction is carried out at a temperature above the melting point of the desired isomerized product generally ranging from about 36° to about 52° C. for the product of II when X is -F, most preferably from about 45° to about 51° C., and about 44° C. to about 50° C. when X is -Cl. The reaction is allowed to proceed until the amount of reactant of formula (I) in the reaction mixture is less than 10,000 ppm. The reaction vessel is then cooled to a temperature, not in excess of its melting point generally ranging from about 17° to about 30° most preferably 25° C. when X is -F and about 42° C. to about 44° C. when X is -Cl. The activated aluminum trichloride derivative is allowed to settle to the bottom of the reaction vessel. Upon settling the organic media is decanted allowing for recovery of the activated catalyst. A thin layer of organic media, generally between about 10 to about 20 weight percent, is permitted to remain with the catalyst. The organic media and catalyst, hereinafter collectively referred to as the "catalytic heel", prevents water vapor from contaminating the catalyst and further facilitates the removal of spent catalyst from the reactor as a fine slurry. By not siphoning off all of the available crude product produced in a given batch, loss of finely divided catalyst is kept to a minimum.

ISOMERIZATION OF CHLOROFLUOROCARBONS

The activated aluminum trichloride derivative prepared as described above is then contacted with fresh chlorofluorocarbon. The catalyst slurry may be transferred either directly to a new reaction vessel or the compound to be isomerized may be added directly to the vessel containing the freshly prepared catalyst.

Chlorofluorocarbons especially suited for the activated aluminum trichloride catalyst are those of the formula:

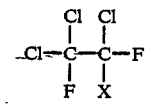
(III)

wherein X is Cl or F.

The desired isomerized product is of the formula:

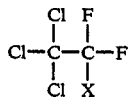
(IV)

The activated aluminum trichloride catalyst employed in the isomerization reaction is normally isolated from a product mixture derived from the chlorofluorocarbon sought to be isomerized. For example, if the desired isomerized product is that represented by a compound of formula (IV) above wherein X is -F, then the activated aluminum trichloride catalyst is generated in the presence of the compound of formula (I) wherein X is -F. However, active catalyst generated by treating anhydrous aluminum trichloride and metal with one chlorofluorocarbon can be used to isomerize a second chlorofluorocarbon.

The isomerization is conducted at a temperature above the melting point of the desired isomerized product, generally, between about 17° C. to about 30° C., preferably about 22° C. to about 28° C., when X is -F and about 42° C. to about 50° C. when X is -Cl. The isomerization is terminated when the amount of starting material in the reaction vessel is less than 450 ppm, preferably when the nonisomerized product is less than 400 ppm. Such conversion normally requires from about 2 hours to about 24 hours, most often 8 hours.

The isomerized product mixture is then permitted to cool to about 2° to about 5° C. above its melting point, wherein the catalyst derivative settles to the bottom of the reaction vessel. The product mixture is then removed. Separation of desired products from the organic phase then proceeds by techniques well known to those skilled in the art, such as distillation. Normally 10 to 20 weight percent of the product mixture is allowed to remain as a slurry with the catalyst to form the catalytic heel. The process may then be repeated until the activated catalyst can no longer effectively render an isomerized product mixture containing less than 450 ppm non-isomerized chlorofluorocarbon. The process is repeated by adding approximately an equivalent weight amount of fresh chlorofluorocarbon (to that weight amount of product mixture removed) to the catalytic heel. Separation of the products from the organic phase can be done collectively on a pool of organic phases from a series of isomerizations or singularly upon the removal of product mixture from catalytic heel.

In general, the weight ratio of chlorofluorocarbon to activated aluminum trichloride catalyst is greater than 16:1. Since the lifespan of the activated catalyst decreases as this ratio increases, commercial practicality dictates this ratio to be probably not greater than 80:1.

The isomerization normally proceeds at atmospheric pressure. However, since the autocatalytic reaction between anhydrous aluminum trichloride and certain chlorofluorocarbons, such as $CCl_2FCClF_2$, can be violent, especially at high temperatures under adiabatic conditions, the activation process may be performed in a suitable high pressure vessel.

EXAMPLE 1

To a 5.0 l glass flask equipped with motor stirrer, thermometer, heating mantle, and reflux condenser with drying tube, was charged 120 g of anhydrous aluminum chloride powder and 6.0 g of PROPACK (a square 0.16 inch 316 stainless steel protruded packing). To the flask was added 3,900 g of $CCl_2FCClF_2$ and vigorous agitation was applied. The mixture was heated to 49°-50° C. (reflux) for 8 hours. Gas chromatography analysis indicated 3,846 ppm $CC_2FCClF_2$.

The mixture was allowed to stand for 2 hours to allow settling of the catalyst. Crude isomerized $CCl_3CF_3$ product was then carefully siphoned off (2,750 g) leaving the active catalyst heel in the bottom of the flask (with a liquid level up to the agitator blades).

EXAMPLE 2

The heating mantle was removed from the 5.0 l flask (example 1), and an adjustable ice bath and addition funnel were added. Over a period of 40 min., 2,750 g of fresh $CCl_2FCClF_2$ was added to the agitated mixture. Reaction temperature was maintained at 22° to 28° C. Upon completion of the addition, the mixture was stirred at 20° C. for 3.5 hours after which gas chromatography analysis indicated only 366 ppm $CCl_2FCClF_2$ remaining.

Agitation was stopped for 2 hours to allow settling of the catalyst bed. The $CCl_3CF_3$ product was siphoned off (2,750 g) and the process repeated (see Table 1).

TABLE 1

ISOMERIZATIONS FROM 316SS ACTIVATED AlCl₃

| Cycle No. | $CCl_2FCClF_2$ reacted (g) | Reaction Time (hrs.) | $CCl_2FCClF_2$ Unreacted, ppm |
|---|---|---|---|
| 1 | 2750 | 3 | 377 |
| 2 | 2750 | 3 | 334 |
| 3 | 2900 | 3 | 341 |
| 4 | 2750 | 3 | 320 |
| 5 | 2800 | 3 | 323 |
| 6 | 2800 | 3 | 309 |
| 7 | 2900 | 3 | 469 |
|   |      | 4 | 332 |
| 8 | 2800 | 4 | 935 |
|   |      | 6 | 342 |
| 9 | 2600 | 3 | 23,000 |
|   |      | 6 | 1,200 |
|   |      | 8 | 406 |

EXAMPLE 3

A 5.0 l flask fitted with motor stirrer, thermometer, heating mantle, and reflux condenser with drying tube, was charged with 96.1 g of anhydrous aluminum trichloride powder, 0.1198 g chromium powder (−200 mesh), 0.0409 g of manganese powder (−325 mesh), and 3,044.5 g of $CCl_2FCClF_2$.

With vigorous agitation, the flask was brought to reflux for 6 hours (48° C.). The mixture was then allowed to agitate for 15 hours at 23°–26° C. At this time the amount of non-isomerized $CCl_2FCClF_2$ had been reduced to 18,400 ppm (IR analysis). The mixture was then brought back to reflux for 7 hours, and then cooled to 27° C. After allowing the catalyst to stand for 16 hours, the amount of non-isomerized $CCl_2FCClF_2$ had dropped to 4,551 ppm (g.c. analysis). The crude product (2127 g) was carefully decanted to avoid disturbing the active catalyst heel.

EXAMPLE 4

The 5.0 l flask (example 3) was fitted with an adjustable ice bath and addition funnel. To the flask was added 2,505 g of fresh $CCl_2FCClF_2$ and agitation begun. Temperature was maintained between 20° and 32° C. After 7 hours reaction, crude product was found to contain 367 ppm $CCl_2FCClF_2$. The catalyst was permitted to settle for 2 hours and 2,100 g of crude $CCl_3CF_3$ product carefully decanted. The process was repeated for a total of 19 cycles (see Table 2).

TABLE 2

ISOMERIZATION REACTIONS FROM Cr/Mn PROMOTED AlCl₃

| Cycle No. | $CCl_2FCClF_2$ Reacted (g) | Reaction Time (hrs.) | $CCl_2FCClF_2$ Unreacted, ppm |
|---|---|---|---|
| 1 | 2505 | 7 | 367 |
| 2 | 2505 | 6 | 310 |
| 3 | 2511 | 3 | 311 |
| 4 | 2400 | 3 | 337 |
| 5 | 2552 | 3 | 320 |
| 6 | 2513 | 3 | 361 |
| 7 | 2512 | 3 | 296 |
| 8 | 2512 | 3 | 333 |
| 9 | 2532 | 3 | 333 |
| 10 | 2506 | 3 | 348 |
| 11 | 2526 | 3 | 368 |
| 12 | 2548 | 4 | 356 |
| 13 | 2507 | 3 | 376 |
| 14 | 2476 | 3 | 334 |
| 15 | 2544 | 3 | 423 |
|    |      | 5 | 352 |
| 16 | 2509 | 3 | 1331 |
|    |      | 5 | 329 |
| 17 | 2524 | 3 | 1184 |
|    |      | 5 | 344 |
| 18 | 2503 | 3 | 4118 |
|    |      | 5 | 495 |
| 19 | 2524 | 3 | 11900 |
|    |      | 5 | 952 |

EXAMPLE 5

A 2.0 l cylinder (Parr bomb) equipped with glass liner and tempered water heating coil was charged 1,000 g of $CCl_2FCClF_2$, 33.3 g of anhydrous aluminum trichloride, 0.04 g of powdered chromium, and 0.01 g of powdered manganese. With vigorous agitation, the mixture was heated from 20° to 50° C. in 42 minutes and pressure was slowly increased. An exotherm then developed which elevated the temperature to 90° C. within 10 minutes and increased pressure to 45 psig. The mixture was allowed to cool and catalyst allowed to settle.

EXAMPLE 6

An insulated beaker with stirrer was charged with 43.5 g of previously prepared catalyst heel (example 5). To the beaker was added 20.2 g of $CCl_2FCClF_2$ and agitation begun. Within 14 minutes, the temperature was allowed to climb from 19° C. until it reached a maximum of 35° C. After 22 minutes stirring, the mixture was sampled and found to contain 92.25% converted $CCl_3CF_3$ (g.c. analysis). Using this data, the heat of isomerization was calculated to be about 3.39 Kcal/mole.

EXAMPLE 7

A 5.0 l flask fitted with a motor stirrer, heating mantle, thermometer, and reflux condenser with drying tube was charged with 120.5 g of anhydrous aluminum trichloride, 0.061 g of powdered manganese (−325 mesh), and 4,008 g of $CCl_2FCClF_2$.

With vigorous agitation, the mixture was heated to reflux for 5 hours (49° C.). Heating was then discontinued and the mixture stirred an additional 13 hours at 28° to 22° C. Gas chromatography analysis indicated approximately 660 ppm of $CCl_2FCClF_2$ in the product mixture. After allowing the catalyst to settle for 2 hours, the crude isomerized product was siphoned off (3100 g), leaving the activated catalyst in the bottom of the flask.

EXAMPLE 8

The 5.0 l flask (example 6) was fitted with an adjustable ice bath and addition funnel. Within 20 minutes, 3100 g of fresh $CCl_2FCClF_2$ was charged (vigorous agitation). After 2.5 hours stirring at 18° to 34° C., the amount of $CCl_2FCClF_2$ in the reaction mixture was approximately 446 ppm. After standing an additional 15 hours, the concentration was 410 ppm. The crude product was then siphoned off (3100 g) and the process repeated (See Table 3).

TABLE 3

ISOMERIZATION REACTIONS OF Mn PROMOTED AlCl₃

| Cycle No. | $CCl_2FCClF_2$ Added/g | Reaction Time (hrs.) | $CCl_2FCClF_2$ Unreacted, ppm |
|---|---|---|---|
| 1 | 3100 | 2.5 | 446 |

TABLE 3-continued

ISOMERIZATION REACTIONS OF Mn PROMOTED AlCl₃

| Cycle No. | CCl₂FCClF₂ Added/g | Reaction Time (hrs.) | CCl₂FCClF₂ Unreacted, ppm |
|---|---|---|---|
|  |  | 17.5 | 410 |
| 2 | 3200 | 2.0 | 326 |
| 3 | 3083 | 3.5 | 710 |
|  |  | 21.0 | 345 |

EXAMPLE 9

A 2.0 l 4-neck flask fitted with motor stirrer, thermometer, and reflux condenser with drying tube was charged with 23.5 g of the resulting catalyst prepared as in Example 3. To the flask was added 256.5 g of CCl₂FCCl₂F and agitation begun. During the first 1.5 hours of stirring the temperature increased from 28° to 34° C. Since the solid product was starting to precipitate, the flask temperature was adjusted to 42° C. and the mixture was then stirred for 2.5 hours. The IR spectrum of the reaction mixture was consistent with nearly total conversion to CCl₃CClF₂.

The invention has been described with reference to its preferred embodiments. Those of ordinary skill in the art may, upon reading this disclosure, appreciate changes or modifications which do not depart from the scope and spirit of the invention as described above or claimed hereafter.

I claim:

1. An activated aluminum trichloride catalyst prepared by the process comprising:
   (i) contacting a chlorofluorocarbon of the formula:

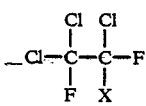 (I)

wherein X is Cl or F,
   with anhydrous AlCl₃ in the presence of a metal;
   (ii) isomerizing said chlorofluorocarbon to the formula:

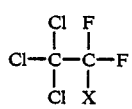 (II)

in the presence of a metal for a time and at a temperature sufficient for the compound of formula (I) to be less than 10,000 ppm;
   (iii) removing the organic layer from the product mixture of step (ii); and
   (iv) recovering the catalytic heel therefrom.

2. The product of claim 1, wherein the weight ratio of chlorofluorocarbon to AlCl₃ is between from about 16:1 to about 80:1.

3. The product of claim 1, wherein said process is conducted in a stainless steel reactor vessel and said metal is leeched from said vessel.

4. The product of claim 1, wherein said metal is selected from the group consisting of chromium, manganese, molybdenum, tungsten and combinations thereof.

5. The product of claim 1, wherein the weight ratio of aluminum chloride to metal is from about 200:1 to about 2000:1.

6. The product of claim 4, wherein said metal is a mixture of chromium and manganese.

7. The product of claim 1, wherein said metal is stainless steel.

8. The product of claim 1, wherein said chlorofluorocarbon is of the formula:

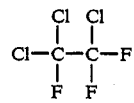

9. A process for isomerizing chlorofluorocarbons comprising:
   (i) contacting a chlorofluorocarbon of the formula:

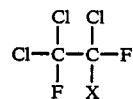 (I)

wherein X is Cl or F with anhydrous AlCl₃ and a metal selected from the group consisting of stainless steel, chromium, manganese, molybdenum, tungsten and combinations thereof;
   (ii) isomerizing said chlorofluorocarbon to the formula:

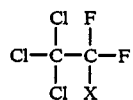 (II)

for a time and at a temperature sufficient for the compound of formula (I) to be less than approximately 10,000 ppm;
   (iii) removing the organic layer from the product mixture of step (ii) and recovering the catalytic heel therefrom;
   (iv) contacting with said catalytic heel, a second chlorofluorocarbon of the formula:

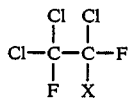 (III)

wherein X is Cl or F;
   (v) isomerizing said chlorofluorocarbon of step (iv) to the formula:

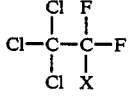 (IV)

for a time and at a temperature sufficient for said second chlorofluorocarbon to be less than 450 ppm in the product mixture;
   (vi) separating at least the majority of the organic phase from the resulting catalytic heel; and
   (vii) isolating the isomerized chlorofluorocarbon of formula (IV) from said organic phase.

10. The process of claim 9, further comprising subsequent to step (vi) successively repeating steps (iv) through (vi).

11. The process of claim 10, wherein the organic phases recovered in repetitive steps (vi) are pooled together after each completion of step (vi).

12. The process of claim 9, wherein the weight ratio of chlorofluorocarbon to catalytic heel in step (iv) is between from about 16:1 to about 80:1.

13. The process of claim 9, wherein the weight ratio of aluminum trichloride to metal in step (i) is from about 200:1 to about 2000:1.

14. The process of claim 9, wherein said X of the compound of formula (I) is fluorine.

15. The process of claim 14, wherein -X of the compound of formula (III) is fluorine.

16. The process of claim 15, wherein the temperature during the isomerization of step (vi) is between from about 17° to about 30° C.

17. The process of claim 9, wherein said chlorofluorocarbon of step (iv) is of the formula:

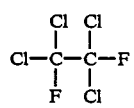

18. The process of claim 17, wherein the temperature during the isomerization of step (v) is from about 42° C. to about 50° C.

19. The process of claim 9, wherein the chlorofluorocarbon of step (i) is of the formula:

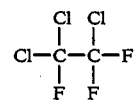

20. The product of claim 4, wherein said metal is chromium.

21. The product of claim 4, wherein said metal is manganese.

22. The product of claim 4, wherein said metal is molybdenum.

23. The product of claim 4, wherein said metal is tungsten.

24. The product of claim 4, wherein said metal is a mixture of chromium and molybdenum.

25. The process of claim 9, wherein said metal is stainless steel.

26. The process of claim 26, wherein said stainless steel is leached from a reactor vessel in which said process is conducted.

27. The process of claim 9, wherein said metal is chromium.

28. The process of claim 9, wherein said metal is manganese.

29. The process of claim 9, wherein said metal is molybdenum.

30. The process of claim 9, wherein said metal is tungsten.

31. The process of claim 9, wherein said metal is a mixture of chromium and manganese.

32. The process of claim 9, wherein said metal is a mixture of chromium and molybdenum.

* * * * *

UNITED STATES PATENT AND TRADEMARK OFFICE
CERTIFICATE OF CORRECTION

PATENT NO. : 4,925,993
DATED : May 15, 1990
INVENTOR(S) : Robert C. Zawalski

It is certified that error appears in the above-identified patent and that said Letters Patent is hereby corrected as shown below:

In column 1, line 67, delete "in situ" and insert --$\underline{in\ situ}$--.

In column 2, line 42, delete "in situ" and insert --$\underline{in\ situ}$--.

In column 3, line 68, delete "nonisomerized" and insert --non-isomerized--.

In column 4, line 47, delete the bold "-50" and insert regular type --  -50  --.

In column 4, line 48, delete "$CC_2FCClF_2$" and insert --$CCl_2FCClF_2$--.

In column 5, line 41, delete "$CC_2FCClF_2$" and insert --$CCl_2FCClF_2$--.

In column 10, line 19, after the word "claim" delete "26" and insert --25-- therefor.

Signed and Sealed this

Twenty-third Day of July, 1991

Attest:

HARRY F. MANBECK, JR.

Attesting Officer    Commissioner of Patents and Trademarks